(12) United States Patent  
Sharp (10) Patent No.: US 12,357,786 B2  
(45) Date of Patent: Jul. 15, 2025

(54) PORTABLE APPARATUS FOR OXYGEN DELIVERY

(71) Applicant: Ian Mackenzie Sharp, Milford, MI (US)

(72) Inventor: Ian Mackenzie Sharp, Milford, MI (US)

( * ) Notice: Subject to any disclaimer, the term of this patent is extended or adjusted under 35 U.S.C. 154(b) by 1016 days.

(21) Appl. No.: 17/364,966

(22) Filed: Jul. 1, 2021

(65) Prior Publication Data

US 2022/0008674 A1  Jan. 13, 2022

Related U.S. Application Data

(60) Provisional application No. 63/049,424, filed on Jul. 8, 2020.

(51) Int. Cl.
| | |
|---|---|
| *A61M 16/00* | (2006.01) |
| *A61M 16/06* | (2006.01) |
| *A61M 16/10* | (2006.01) |
| *A61M 16/20* | (2006.01) |

(52) U.S. Cl.
CPC .... *A61M 16/1005* (2014.02); *A61M 16/0003* (2014.02); *A61M 16/06* (2013.01); *A61M 16/105* (2013.01); *A61M 16/201* (2014.02); *A61M 2016/0027* (2013.01); *A61M 2205/6081* (2013.01); *A61M 2209/088* (2013.01)

(58) Field of Classification Search
CPC .............. A61M 16/00; A61M 16/1005; A61M 16/125; A61M 16/06; A61M 16/105; A61M 16/0666; A61M 16/0683; A61M 25/02; A61M 16/207; A61M 16/0841; A63B 71/085; A62B 2071/086

See application file for complete search history.

(56) References Cited

U.S. PATENT DOCUMENTS

| | | | |
|---|---|---|---|
| 5,887,585 A | 3/1999 | Dusenbery | |
| 6,155,258 A * | 12/2000 | Voege | A62B 7/02 128/205.21 |
| 6,220,244 B1 | 4/2001 | McLaughlin | |
| 6,364,161 B1 | 4/2002 | Pryor | |
| 6,394,088 B1 * | 5/2002 | Frye | A61M 16/207 128/205.24 |

(Continued)

FOREIGN PATENT DOCUMENTS

WO    WO-2019173869 A1 *  9/2019  ............. A61F 5/566

OTHER PUBLICATIONS

Shock Doctor mouth guard publication (published or offered for sale on or before Feb. 26, 2020), https://www.unitedspb.com/shock-doctor.

(Continued)

*Primary Examiner* — Margaret M Luarca  
*Assistant Examiner* — Sarah B Lederer  
(74) *Attorney, Agent, or Firm* — Harness, Dickey & Pierce PLC (57) ABSTRACT

A portable apparatus for oxygen delivery includes a receptacle, a mouthpiece and a tube. In another aspect the mouthpiece includes a first fluid channel for a first fluid and a second fluid channel for a second fluid that is different from the first fluid. In a further aspect, the portable apparatus includes a receptacle, a mouthpiece and a tube in which the mouthpiece includes a teeth engagement portion, a lip engagement portion and a lip protection portion.

17 Claims, 8 Drawing Sheets

(56) References Cited

U.S. PATENT DOCUMENTS

| | | | |
|---|---|---|---|
| 7,708,016 | B2 | 5/2010 | Zaiser et al. |
| 9,333,413 | B2 | 5/2016 | Evans et al. |
| 10,610,658 | B2 | 4/2020 | Tiep et al. |
| 2004/0194829 | A1 | 10/2004 | Zaiser et al. |
| 2006/0112962 | A1* | 6/2006 | Tebbutt ................. A61M 16/06 128/206.29 |
| 2008/0173304 | A1 | 7/2008 | Zaiser et al. |
| 2009/0212081 | A1 | 8/2009 | Liang et al. |
| 2013/0032150 | A1 | 2/2013 | Zaiser et al. |
| 2014/0276171 | A1* | 9/2014 | Hestness ................. A61B 5/097 600/249 |
| 2016/0331923 | A1 | 11/2016 | Zaiser et al. |
| 2016/0354231 | A1* | 12/2016 | Thornton ................. A61F 5/566 |
| 2017/0209300 | A1* | 7/2017 | Radmand .......... A61M 16/0816 |
| 2017/0266401 | A1* | 9/2017 | Arden ................. A61B 17/025 |
| 2018/0361107 | A1* | 12/2018 | Darling ............. A61M 16/0677 |
| 2019/0015726 | A1 | 1/2019 | Turkbas |

OTHER PUBLICATIONS

Drive Medical owners manual (published on or before Feb. 20, 2020).

O2Xigeno Pause publication (published on or before Feb. 20, 2020).

Nathan internet site (published 2018), https://www.unitedspb.com/nathan.

Drive Medical—Devillbus catalog (published on or before Feb. 20, 2020).

Airofit user manual (published 2019).

\* cited by examiner

PORTABLE APPARATUS FOR OXYGEN DELIVERY

CROSS-REFERENCE TO RELATED APPLICATION

The application claims the benefit of U.S. Provisional Application No. 63/049,424, filed on Jul. 8, 2020. The entire disclosure of the above application is incorporated herein by reference.

FIELD

The present disclosure relates to an oxygen delivery apparatus and more particularly to a portable apparatus for oxygen delivery to be used during an activity.

BACKGROUND AND SUMMARY

Conventional portable oxygen cylinders are used to deliver oxygen to a user who has medical problems when the user is performing passive daily activities such as sleeping or sitting in a chair; these oxygen cylinders are often mounted to wheeled carts. Furthermore, some traditional cylinders are part of small and crude handheld units that have a small rigid end for insertion into the user's mouth for a single injection of oxygen for use at high altitudes. However, such portable oxygen delivery apparatuses are not suitable for easy use while performing vigorous activities such as jogging and bicycling where the user benefits greatly from an increased and regularly flowing amount of oxygen to the body. Furthermore, such known portable oxygen cylinders are not easily adaptable to different activities since they require one of the user's hands to pull the cart or hold the unit. The portable oxygen cylinders are also not refillable, and are discarded after the cylinders are depleted, which can be an environmental concern. These traditional devices are also not in conformity with the users' mouth to simultaneously allow high volume air flow breathing during energetic activities.

Another traditional device is disclosed in U.S. Patent Publication No. 2018/0361107 entitled "Portable Oxygen System" which published to Darling on Dec. 20, 2018, and is incorporated by reference herein. This device employs a nozzle attached to a hose with the nozzle compressed between the user's teeth. The nozzle, however, is unsuitable for vigorous exercise since it is likely to fall out of the user's mouth and it blocks the airway to the ambient air especially during exhalation. The hose on the Darling device is retractable on a coil device and is used on a need infusion basis, similar to the aerosol can type and provides a few breaths as an aid to temporary exercise recovery.

In accordance with the present invention, a portable apparatus for oxygen delivery is provided. In one aspect, the portable apparatus includes a receptacle, a mouthpiece and a tube wherein the mouthpiece includes a first fluid channel for a first fluid and a second fluid channel for a second fluid that is different from the first fluid. In another aspect, the portable apparatus includes a receptacle, a mouthpiece and a tube wherein the mouthpiece includes a teeth engagement portion, a lip engagement portion and a lip protection portion. A further aspect includes a valve for the receptacle that is moveable between a first position in which high pressure fluid in a first space in the receptacle is prevented from flowing to a second space of the receptacle, and a second position in which high pressure fluid in the first space is allowed to flow to the second space. A method of using a portable oxygen delivery apparatus is also provided.

The portable apparatus according to the present disclosure is advantageous over conventional devices. For example, the portable apparatus of the present disclosure can be used by the user to increase their oxygen intake and thus oxygen blood levels when performing a vigorous activity such as jogging and bicycling. Another benefit of the portable apparatus of the present disclosure is that the portable apparatus is easily adaptable to different activities. The present apparatus also conforms to the user's mouth but while allowing substantially simultaneous high volume air inhalation and exhalation from the mouth without significant obstruction. The present apparatus is advantageously easy to wear and/or use in a hands-free manner, is light weight and is refillable. Additional advantages and benefits will become apparent from the following description and appended claims, taken in conjunction with the accompanying drawings.

DRAWINGS

The drawings described herein are for illustrative purposes only of selected embodiments and not all possible implementations, and are not intended to limit the scope of the present disclosure.

FIG. 1a is a perspective view showing an exemplary portable apparatus for oxygen delivery accordingly to the present disclosure;

FIG. 1b is a side elevation view showing a conserver device of the portable apparatus of FIG. 1a;

DETAILED DESCRIPTION

Figures 1A, 1B:
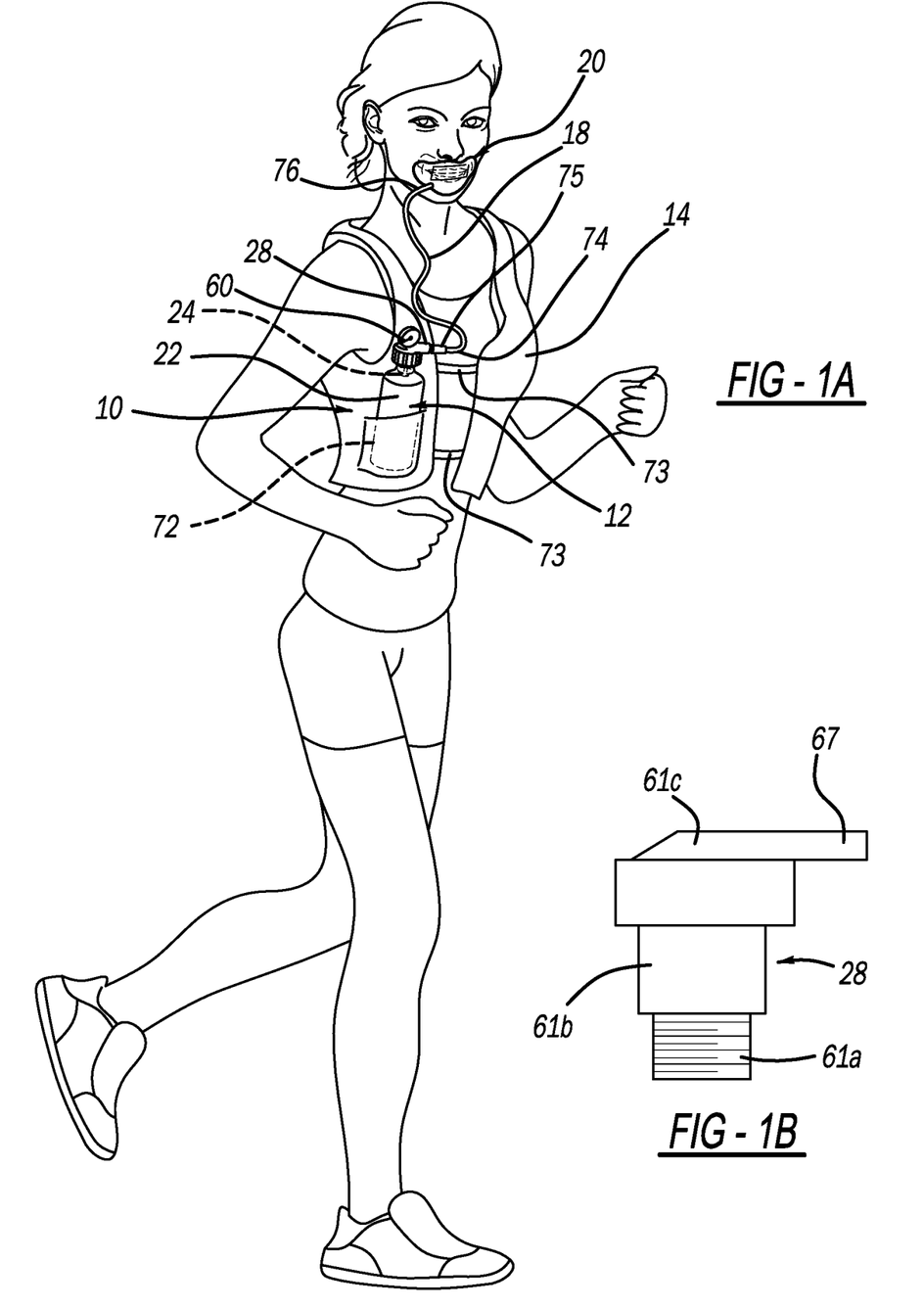

FIG. 1a shows a portable apparatus 10 for oxygen delivery to a user. Portable apparatus 10 can be used while the user is performing vigorous activity such as exercising where a high volume of ambient air is also being inhaled and exhaled through the user's mouth. For example, the user may be jogging as shown in FIG. 1a. In other embodiments, the user may be bicycling, walking, lifting weights, or performing any other activity in which the user may benefit from oxygen delivery to his or her body. Portable apparatus 10 includes a receptacle or bottle 12, a wearable device 14, a flexible tube 18 and a mouthpiece 20.

Figure 2:
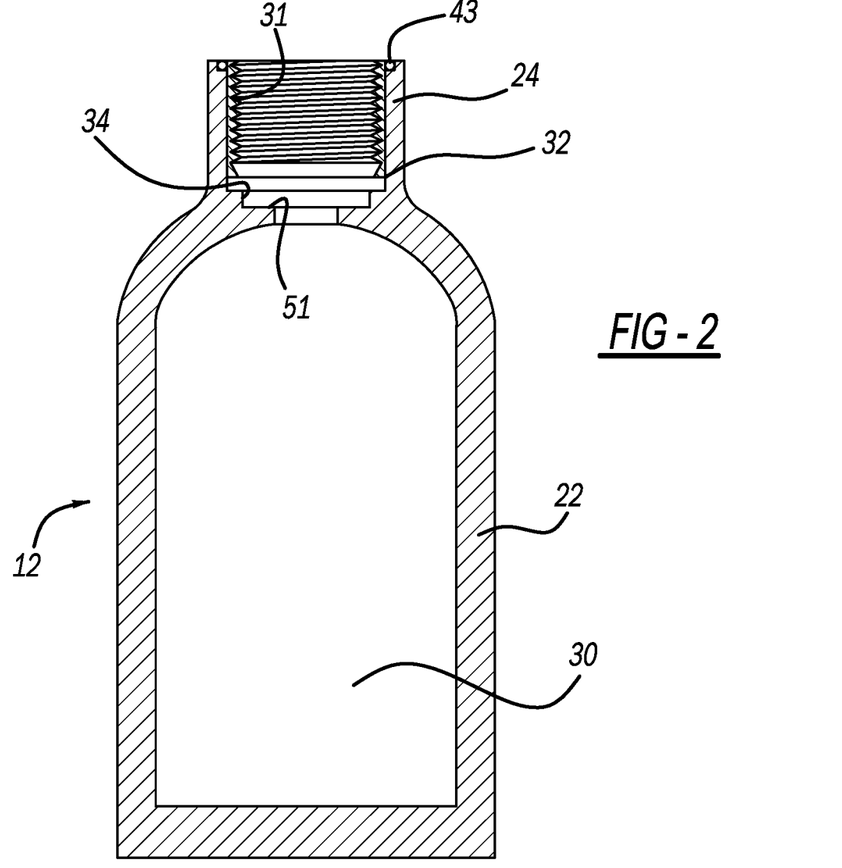
FIG. 2 is a cross-sectional view showing a bottle of the portable apparatus with a valve of the bottle omitted for further clarity.
Figure 8:
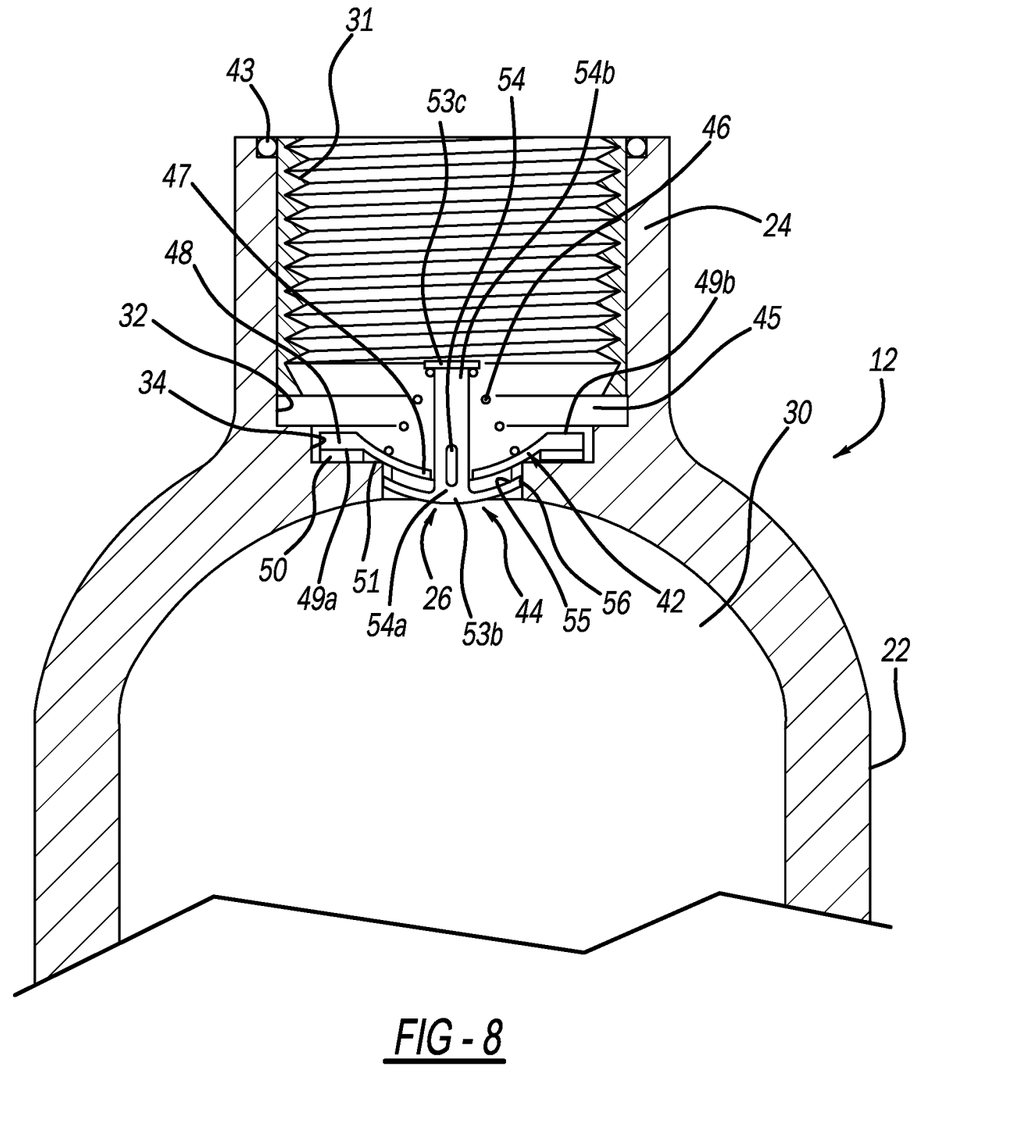
FIG. 8 is a partially fragmentary side showing the bottle of the portable apparatus with the valve of the bottle disposed therein.

With reference to FIGS. 1a, 2 and 8, receptacle 12 includes a body portion 22, a neck portion 24, a valve 26 (FIG. 8), and an integrated pressure regulator and conserver device 28 (FIG. 1a). Body portion 22 defines a space 30 containing high pressure oxygen. For example, the oxygen contained within space 30 may have a pressure between 2500 pounds per square inch (psi) and 3500 pounds per square inch (psi), and more preferably a pressure of 3000 pounds per square inch (psi). Neck portion 24 includes an annular groove 32 formed in an inner cylindrical surface 34 of neck portion 24 and annular groove formed in an axial end surface of neck portion 24. A sealing member 43 (O-ring) is disposed within the annular groove formed in the axial end surface of neck portion 24 and is sealingly engaged with the conserver device 28 to prevent the pressurized fluid in receptacle 12 from escaping. An insert 31 having female threads is coupled to neck portion 24, and is configured to be threadably engaged with male threads of conserver device 28. Insert 31 is also configured to abut against retaining clip 45, thereby acting as a safety feature to retain clip 45 in position.

Figure 3:
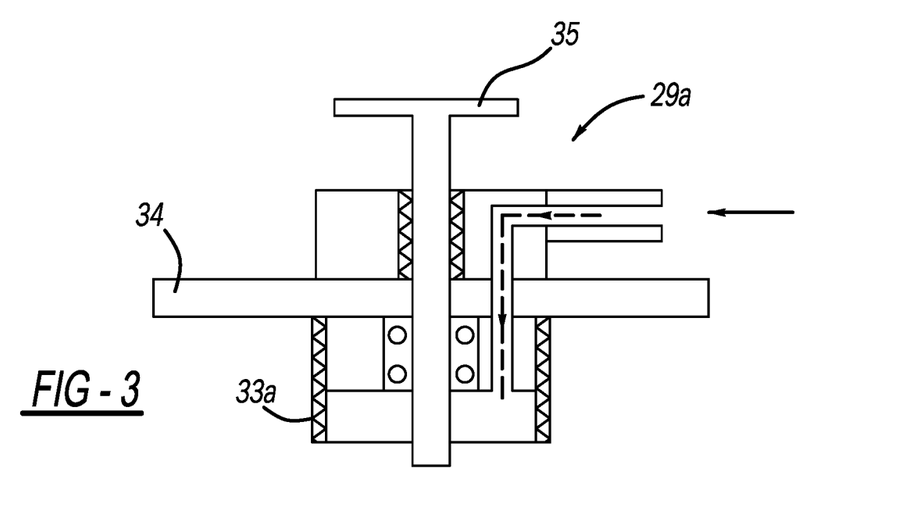
FIG. 3 is a diagrammatic side view showing an exemplary filling system for filling the bottle of the portable apparatus.

Receptacle 12 may be refilled with oxygen using an oxygen filling system 29a, 29b. For example, as shown in FIG. 3, oxygen filling system 29a can be used to refill receptacle 12. That is, threads of insert 31 are threadably engaged with male threads 33a of filling system 29a. Tightening knob 34 ensures that receptacle 12 is secured to filling system 29a. Once receptacle 12 is secured to filling system 29a, a plunger 35 is moved from a first position in which plunger 35 is not engaged with valve 26 of receptacle 12 to a second position in which plunger 35 is engaged with valve 26. When plunger 35 is in second position, plunger 35 moves valve 26 from closed position to open position such that high pressure oxygen from an oxygen source may flow through filling system 29a and into space 30 of body portion 22.

Figure 4:
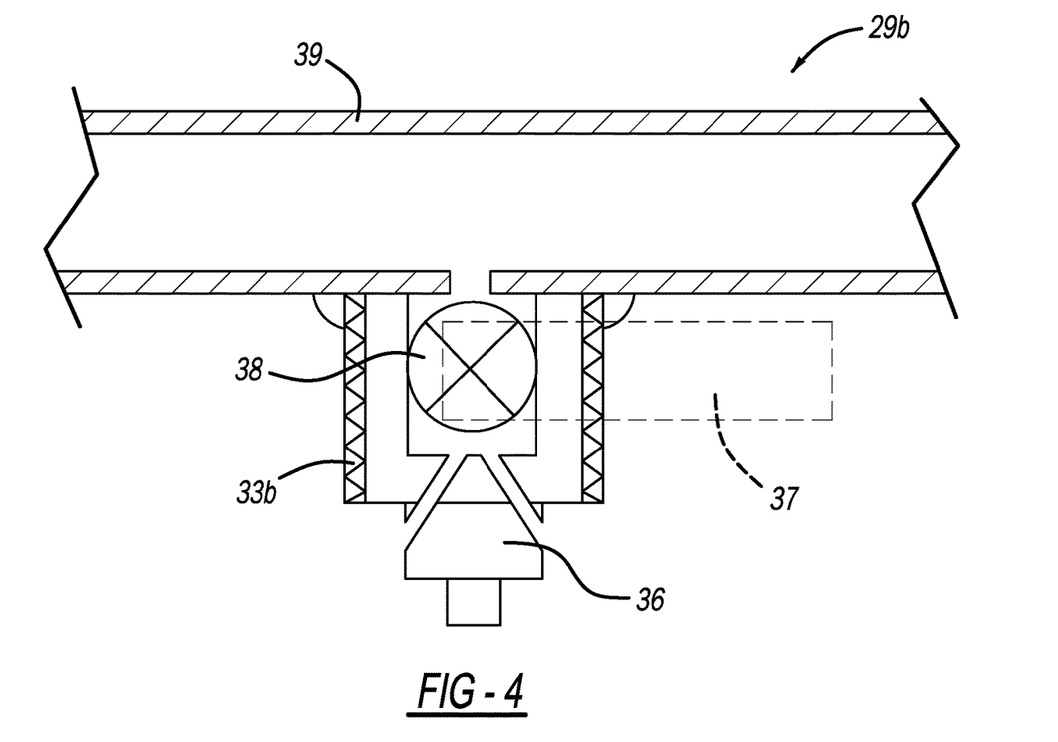
FIG. 4 is a diagrammatic side view showing an exemplary filling system for filling the bottle of the portable apparatus.

In another example, as shown in FIG. 4, oxygen filling system 29b can be used to refill receptacle 12. That is, threads of insert 31 are threadably engaged with male threads 33b of filling system 29b. Once receptacle 12 is secured to filling system 29b, pin 36 moves valve 26 of receptacle 12 from the closed position to the open position. Lever 37 may then be actuated from a first position in which valve 38 prevents high pressure oxygen from flowing from a manifold 39 through filling system 29b to a second position in which valve 38 allows high pressure oxygen from manifold 39 to flow through filling system 29b and into space 30 of body portion 22.

Valve 26 is disposed within neck portion 24 of receptacle 12 and is movable between a first position (i.e., closed position) in which high pressure oxygen within space 30 of body portion 22 is prevented from flowing to conserver device 28, and a second position (i.e., open position) in which high pressure oxygen within space 30 of body portion 22 is allowed to flow to conserver device 28. High pressure oxygen within space 30 of body portion 22 biases valve 26 in the first position when conserver device 28 is removed from receptacle 12. In this way, high pressure oxygen within space 30 is prevented from escaping receptacle 12. When conserver device 28 is attached to receptacle 12, conserver device 28 moves valve 26 to the second position such that high pressure oxygen within space 30 is allowed to flow from space 30 to conserver device 28.

Figure 7:
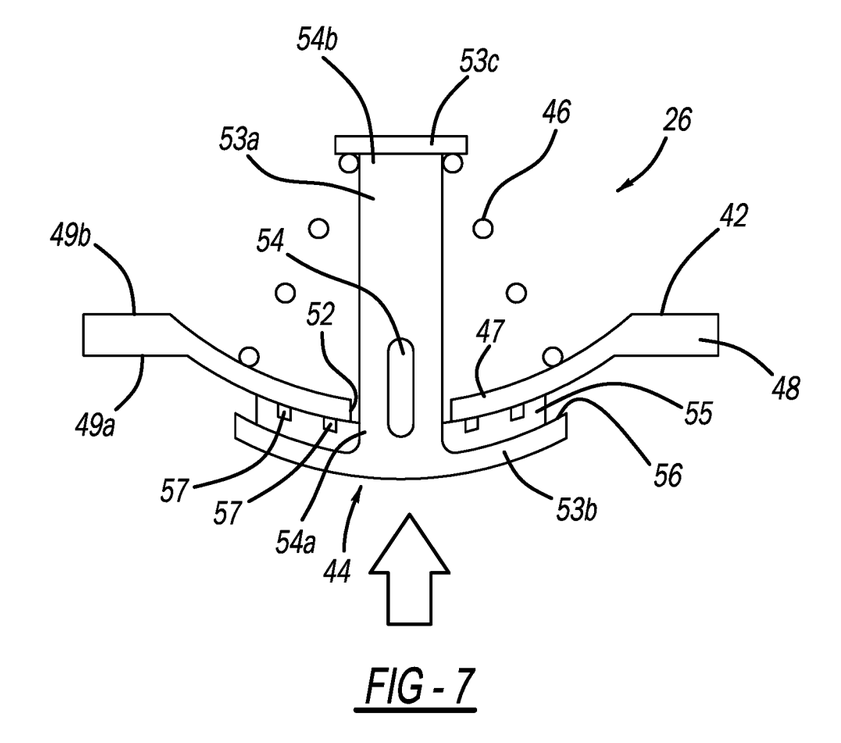
FIG. 7 is a front elevational view showing the valve of the bottle.

FIGS. 7 and 8 illustrate valve 26 which includes a plate 42, a pin 44, and a biasing member 46. Plate 42 includes an arcuate-shaped central portion 47 and a flange portion 48 extending around and radially outwardly from a periphery of central portion 47. A bottom surface 49a of flange portion 48 is sealingly engaged with a sealing member 50 (O-ring) disposed on an annular land 51 of receptacle 12, thereby preventing high pressure oxygen within space 30 of body portion 22 from escaping receptacle 12. Plate 42 is held in place by a retaining clip 45 received in groove 32 of neck portion 24 and configured to engage a top surface 49b of flange portion 48.

Pin 44 extends through an opening 52 formed in central portion 47 of plate 42 and is moveable between a first position in which high pressure oxygen within space 30 of body portion 22 is prevented from flowing to conserver device 28, and a second position in which high pressure oxygen within space 30 of body portion 22 is allowed to flow to conserver device 28. High pressure oxygen within space 30 of body portion 22 biases pin 44 in the first position when conserver device 28 is removed from receptacle 12. Pin 44 includes a shaft portion 53a, a head portion 53b and a flange portion 53c. Shaft portion 53a extends through opening 52 of plate 42 and includes one or more elongated slots 54 formed therein. When pin 44 is in the first position, slots 54 are located out of space 30 of body portion 22, thereby preventing high pressure fluid in space 30 from flowing to conserver device 28. When pin 44 is in the second position, slots 54 are located within space 30 of body portion 22, thereby allowing high pressure fluid in space 30 to flow into conserver device 28.

Head portion 53b has an arcuate shape and extends radially outwardly from a first axial end 54a of shaft portion 53a. A sealing member 55 is coupled to an inner surface 56 of head portion 53b and is sealingly engaged with a plurality of annular protrusions 57 formed on central portion 47 of plate 42 when pin 44 is in the first position. When pin 44 is in the second position, sealing member 55 is spaced apart from protrusions 57. Flange portion 53c extends radially outwardly from a second axial end 54b of shaft portion 53a that is opposite first axial end 54a. Flange portion 53c acts as a stop member to prevent pin 44 from dropping into space 30 of body portion 22. That is, flange portion 53c has a diameter than is greater than a diameter of opening 52 of central portion 47 such that flange portion 53c is prevented from entering into opening 52.

Biasing member 46 is coupled to flange portion 53c at one end and to central portion 47 of plate 42 at another end, and further biases pin 44 toward the first position. When conserver device 28 is coupled to receptacle 12, conserver device 28 pushes down on pin 44, thereby overcoming the force of biasing member 46 and high pressure oxygen in space 30. In this way, pin 44 is moved to the second position and high pressure oxygen is allowed to flow from space 30 to conserver device 28.

As shown in FIG. 1a, conserver device 28 is coupled to neck portion 24 of receptacle 12 and regulates the flow of oxygen from space 30 of body portion 22 to the user (via tube 18 and mouthpiece 20). Conserver device 28 delivers oxygen when the user inhales, thus, increasing efficiency of the apparatus 10. As shown in FIG. 1b, conserver device 28 includes an attachment portion 61a, a body portion 61b and an end portion 61c. Attachment portion 61a extends downwardly from body portion 61b and is a generally cylindrical shape. Attachment portion 61a includes male threads that are configured to be threadably engaged with female threads of insert 31. In this way, the conserver device 28 may be removably coupled to neck portion 24 of receptacle 12. When conserver device 28 is removed from neck portion 24, receptacle 12 may be filled with oxygen as described above. When the conserver device 28 is coupled to neck portion 24, oxygen within receptacle 12 is prevented from escaping. Because conserver device 28 can be conveniently removed from neck portion 24 to fill the receptacle 12 with oxygen, fill ports or any other sockets used to fill receptacle 12 with oxygen are not required, thereby reducing overall size and weight of conserver device 28. Body portion 61b is made of a metal material and is disposed between attachment portion 61a and end portion 61c.

End portion 61c includes a fluid delivery port 67 that is removably coupled to flexible tube 18. In this way, when fluid delivery port 67 and tube 18 are coupled to each other, oxygen in conserver device 28 is allowed to flow to tube 18 upon inhalation of the user. End portion 61c may include indicia that signifies the flow rate of conserver device 28. For example, end portion 61c may be a specific color (e.g., blue), which, in turn, is associated with a specific flow rate (e.g., 2 liters per minute). Thus, conserver device 28 operates at a single flow rate. In some configurations, conserver device 28 may be adjustable among a plurality of flow rates. It is understood that the conserver device 28 makes up approximately 20% of the receptacle 12. Other methods and configurations of conserver device 28 are contemplated. For example, a conserver design that is disclosed in U.S. Pat. No. 8,307,828 entitled "Pneumatic Single-Lumen Medical Gas Conserver" which published to Inovo, Inc. on Nov. 12, 2012, and is incorporated by reference herein is also contemplated.

Figure 5:
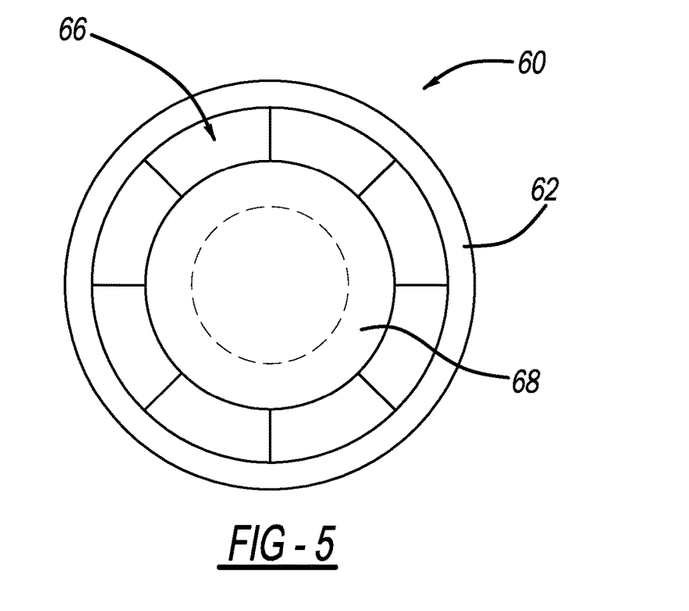
FIG. 5 is a front view showing a pressure indicator of the bottle of the portable apparatus.
Figure 6:
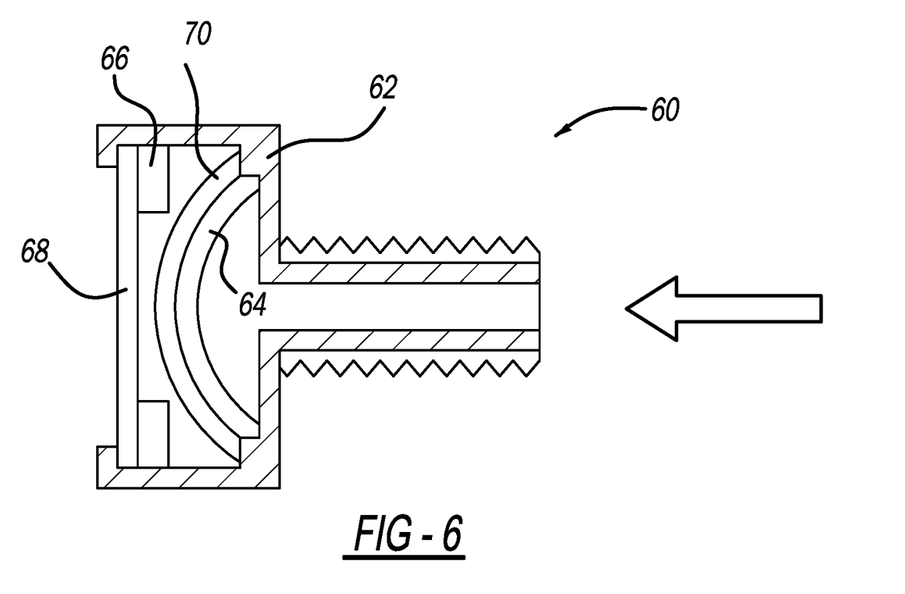
FIG. 6 is a diagrammatic side view showing the pressure indicator of the bottle of the portable apparatus.

A pressure indicator or gauge 60 is operatively coupled to end portion 61c of conserver device 28 and is configured to measure the pressure of oxygen within conserver device 28. With reference to FIGS. 5 and 6, pressure gauge 60 includes a housing 62, a diaphragm 64, a segmented color gauge 66 and lens 68. Diaphragm 64, segmented color gauge 66 and lens 68 are disposed within housing 62. Diaphragm 64 is made of a steel material, for example, and is coupled (e.g., staked) to housing 62. Diaphragm 64 is coated with a mechanochemical polymer material 70 such as a spiropyran-mechanophore material. In this way, when oxygen in conserver device 28 flows to pressure gauge 60, the oxygen deforms diaphragm 64, which causes diaphragm 64 to bend outwardly toward lens 68 coupled to housing 62. When diaphragm 64 deforms, material 70 coated on diaphragm 64 changes color based on the strain on diaphragm 64. The color of material 70 may be matched with a color on color gauge 66 to indicate the pressure of oxygen within conserver device 28. That is, each color on the segmented color gauge 66 has a corresponding pressure or range of pressures associated with it such that the color of material 70 can be matched with a color on color gauge 66 to indicate the pressure of oxygen within conserver device 28.

The user wears wearable device or garment 14 during the activity. Wearable device 14 includes one or more pockets 72 formed therein. Wearable device 14 also includes one or more straps 73 that facilitate retention of wearable device 14 on the user while performing the activity; optionally, a clip or hook-and-loop fastener can removably secure the hose to an upper section of the wearable garment. Receptacle 12 is securely received in a corresponding pocket 72 such that receptacle 12 minimally impacts the user while the user is performing the activity. Wearable device 14 shown in FIG. 1a is preferably a textile workout vest but may alternately be a jacket, shirt, frontpack or backpack. In some configurations, wearable device 14 may be a belt or any other device that may securely receive receptacle 12 in a hands-free manner while the user is performing the activity.

Flexible tube 18 has a first end 74 that is coupled to a port 75 of conserver device 28 and a second end 76 that is coupled to mouthpiece 20. In this way, first end 74 is fluidly coupled to conserver device 28 and second end 76 is fluidly coupled to mouthpiece 20, thereby allowing oxygen gas in conserver device 28 to flow to mouthpiece 20 and into the mouth of the user when the user inhales while performing an activity.

Figure 9:
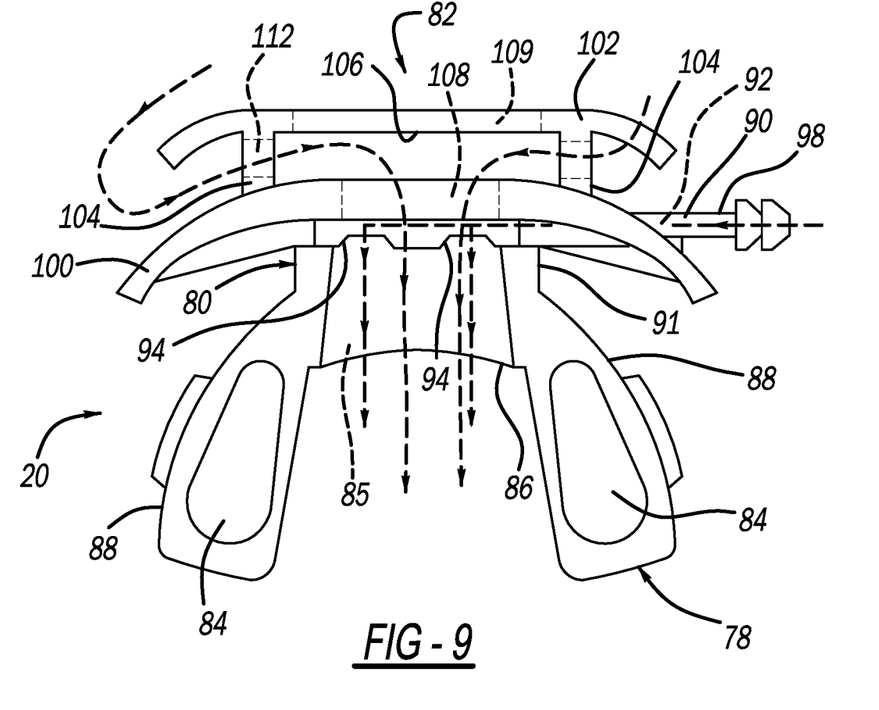
FIG. 9 is a top elevational view showing a mouthpiece of the portable apparatus.
Figure 10:
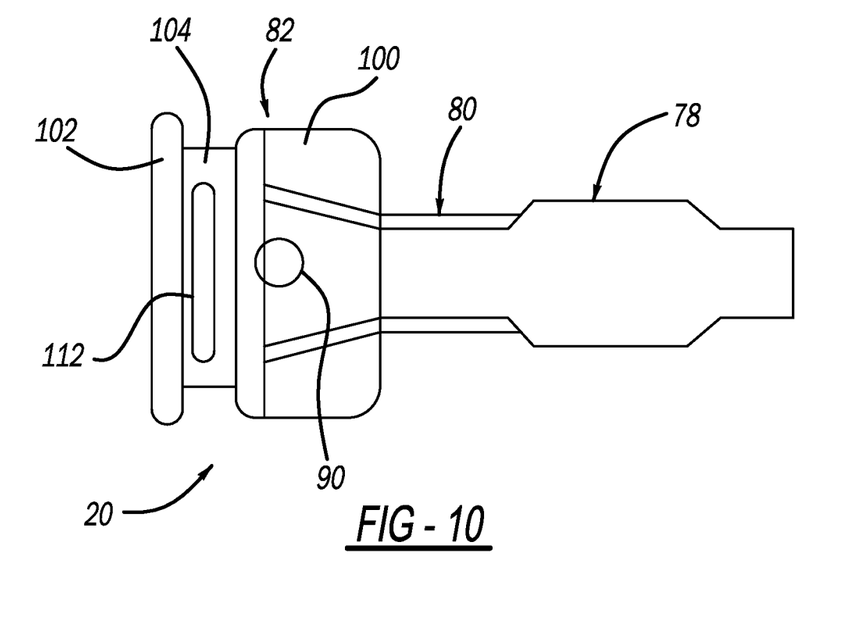
FIG. 10 is a side elevational view showing the mouthpiece of the portable apparatus.
Figure 11:
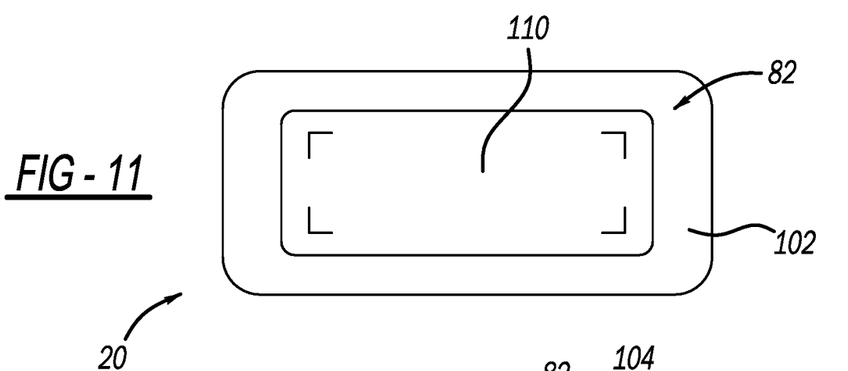
FIG. 11 is a front elevational view showing the mouthpiece of the portable apparatus.
Figure 12:
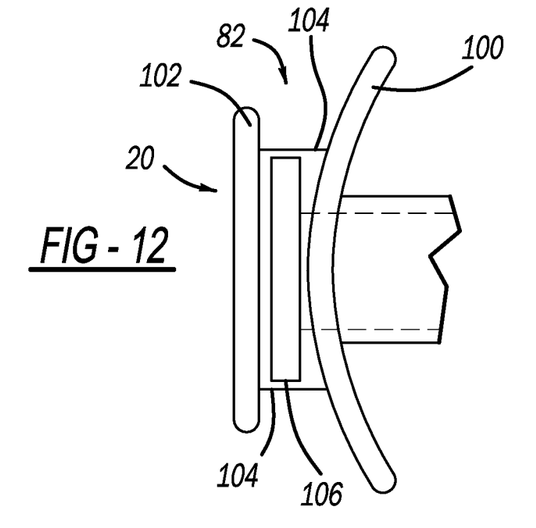
FIG. 12 is top elevational view showing the mouthpiece of the portable apparatus.

With reference to FIGS. 9-12, mouthpiece 20 may be made of a polymeric material and includes a teeth engagement portion 78, a lip engagement portion 80 and a lip protector portion 82. Teeth engagement portion 78 is configured to be clenched by the user and includes a plurality of protrusions 84 and a mixing chamber 85 (FIG. 9). The protrusions 84 facilitate engagement with the user's teeth. In some configurations, other structural features may be used instead of, or in addition to, protrusions 84 to facilitate engagement with the user's teeth.

Teeth engagement portion 78 also includes an inner surface 86 and a lateral or outer surface 88. Teeth engagement portion 78 may be made of a moldable plastic material, for example, that when heated can conform to a user's teeth pattern. The inner surface 86 generally faces toward the tongue of the user and the lateral surface 88 generally faces toward an inner surface of the user's cheeks. Ambient air and oxygen from conserver device 28 mix in mixing chamber 85 before the gas enters into the mouth of the user.

Lip engagement portion 80 is disposed between teeth engagement portion 78 and lip protector portion 82. An oxygen bar 90 is made of a polymeric material having a greater hardness than the polymeric material of mouthpiece 20 and is formed (e.g., molded) in lip engagement portion 80 of mouthpiece 20. Oxygen bar 90 extends in a transverse direction relative a longitudinal direction of mouthpiece 20 and protrudes outwardly from a lateral side 91 of lip engagement portion 80. Furthermore, oxygen bar 90 defines a fluid channel 92 that is fluidly coupled to mixing chamber 85 via a plurality of distribution openings 94 formed in a surface 96 of oxygen bar 90. Openings 94 also face toward inner surface 86 of teeth engagement portion 78. An end 98 of oxygen bar 90 is coupled to second end 76 of tube 18 so that fluid channel 92 is fluidly coupled to conserver device 28 via tube 18. Other methods and configurations of introduction of oxygen to the airway path through the mouthpiece 20 are contemplated. For example, a mouthpiece design that is disclosed in U.S. Patent Publication No. 2019/0015726 entitled "Mouthguard Including Breathing Channels" which published to Shock Doctor, Inc. on Jan. 17, 2019, and is incorporated by reference herein is also contemplated.

Lip protector portion 82 extends from lip engagement portion 80 and at least partially covers the lips of the user. Lip protector portion 82 includes an inner or lip protection section 100, an outer section 102 and lateral sides 104 that cooperate to define a rectangular shaped pocket 106. Inner protection section 100 at least partially covers the lips of the user and defines a fluid channel 108 extending therethrough. Moreover, fluid channel 108 is fluidly coupled to mixing chamber 85 of teeth engagement portion 78. Outer section 102 defines an opening 109 that extends therethrough and is fluidly coupled to fluid channel 108 via pocket 106. A plate 110 is removably coupled to outer section 102. In this way, ambient air is allowed to flow through opening 109 and into fluid channel 108 when plate 110 is coupled to outer section 102 and is prevented from flowing through opening 109 when plate 110 is removed from outer section 102.

Figure 13:
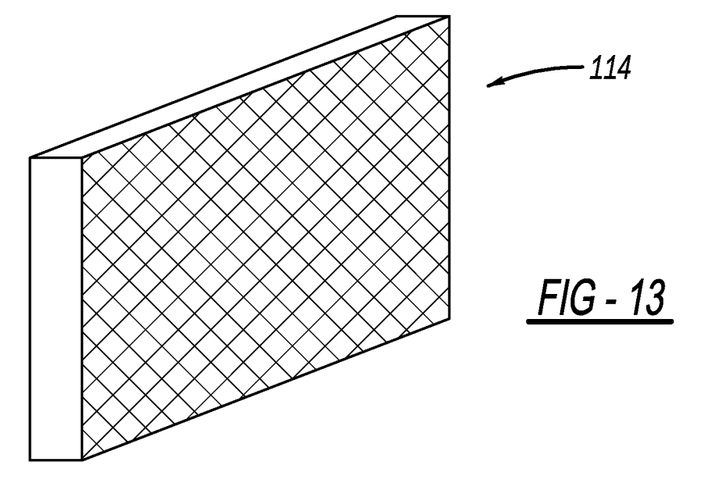
FIG. 13 is a perspective view showing a filter for the mouthpiece of the portable apparatus.

Lateral sides 104 define an elongated opening 112 (FIGS. 9 and 12) that extends therethrough and is fluidly coupled to fluid channel 108 via pocket 106. As shown in FIG. 13, a filter 114 such as a carbon activated filter or high-efficiency particulate air (HEPA) filer, for example, is received in pocket 106 such that ambient air flowing through opening 112 in lateral sides 104 and opening 109 in outer section 102 (when plate 110 is detached from outer section 102) passes through filter 114 prior to flowing to fluid channel 108. In this way, insects, viruses, bacteria, volatile organic compounds (VOCs), dust and other contaminants are prevented from flowing into the mouth of the user. This filter is especially beneficial when the user is riding a fast moving bicycle or the like to prevent the contaminants from entering the otherwise always open ambient air entrance to the mouthpiece.

Figure 14:
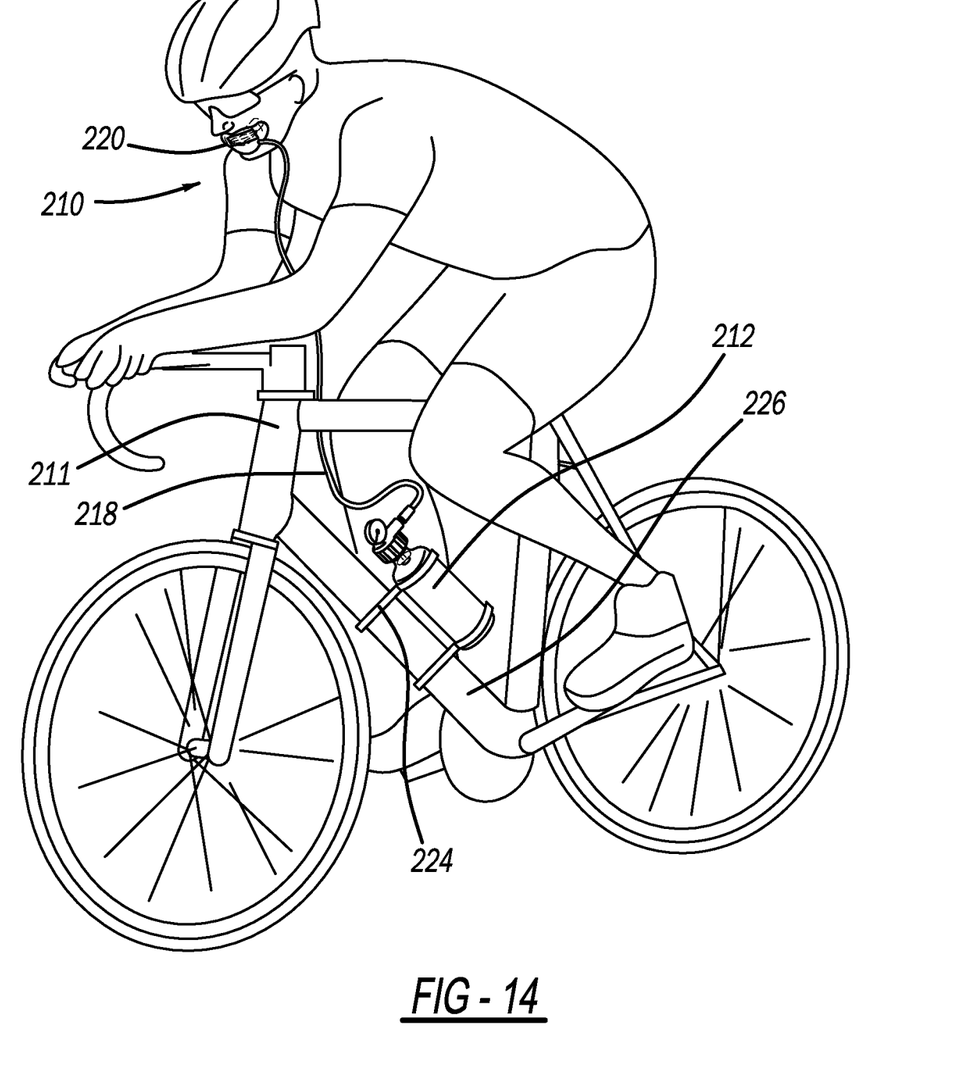
FIG. 14 is a perspective view showing an alternate embodiment of the portable apparatus mounted to a bicycle.

FIG. 14 shows a portable apparatus 210 delivering oxygen to a user while the user is riding a bike 211. Portable apparatus 210 includes a receptacle or bottle 212, a flexible tube 218 and a mouthpiece 220. Receptacle 212, tube 218 and mouthpiece 220 may be similar or identical to receptacle 10, tube 18 and mouthpiece 20, respectively, described above, and therefore, will not be described again in detail. Receptacle 212 may be removably received in a bottle holder 224 fixed to a frame 226 of the bike 211.

With continued reference to FIGS. 1-13, operation of the apparatus 10 will now be described in detail. Prior to the user performing an activity, the user puts on wearable device 14, places filled receptacle 12 in pocket 72 of wearable device 14, and inserts mouthpiece 20 into his or her mouth.

During the activity, when the user inhales, oxygen flows through fluid channel 92 of oxygen bar 90 via tube 18 and conserver device 28 and into mixing chamber 85, and ambient air flows through fluid channel 108 of lip protector portion 82 and into mixing chamber 85. Oxygen and ambient air in mixing chamber 85 mixes with each other before entering the mouth of the user. In this way, the user breathes in a higher percentage of oxygen compared to the amounted contained in only inhaling ambient air, which improves the user's levels of stamina/endurance and allows the user's body to recover more quickly after performing the activity. It should be understood that oxygen is restricted from flowing through fluid channel 108 of lip protector portion 82 and ambient air is restricted from flowing through the fluid channel 92 of oxygen bar 90.

One of the benefits of apparatus 10 of the present disclosure is that apparatus 10 is portable and can be used by the user to increase their oxygen intake when performing an activity. Another benefit of apparatus 10 of the present disclosure is that apparatus 10 is easily adaptable to different activities. For example, wearable device 14 can be removed when the user is performing a stationary activity (e.g., riding an exercise bike). In such example, receptacle 12 may be disposed in a bottle holder coupled to the exercise bike.

While various embodiments have been disclosed, other variations are envisioned. For example, mouthpiece 20 may be used intermittingly as opposed to continuously when performing the activity. The mouthpiece 20 can also be held in place by an elastic band around the head of the user. Oxygen bar 90 may protrude out a bottom or a top of lip engagement portion 80 instead of lateral side 91. In another example, oxygen bar 90 may be formed in lip protector portion 82 instead of in lip engagement portion 80. In yet another example, bottle 12 may have a different shape from that shown for further comfort to the user; for example, one or more exterior surfaces of the bottle can have a concave curved shape to more closely conform to the user's body and to reduce relative movement during the vigorous activity. Various features may be interchanged between figures and embodiments, and the claims can be multiply dependent on each other in any and all combinations. The above description is merely exemplary in nature and, thus, variations that do not depart from the gist of the invention are intended to fall within the spirit and scope of the present invention.

What is claimed is:

1. A portable apparatus for pressurized gas delivery, the apparatus comprising:
    a portable receptacle defining a space containing the pressurized gas;
    a pressure regulator and a conserver fluidly coupled to the portable receptacle;
    a mouthpiece defining a first fluid channel and a second fluid channel;
    a plate removably coupled to the mouthpiece; and
    a tube having a first end fluidly coupled to the receptacle and a second end fluidly coupled to the first fluid channel of the mouthpiece;
    wherein the tube is configured to provide pressurized gas in the receptacle to the first fluid channel of the mouthpiece;
    wherein the plate is configured to allow or restrict ambient air flow into the second fluid channel of the mouthpiece; and
    wherein the conserver comprises a pressure gauge including a metallic diaphragm located within a housing, the diaphragm is coated with a polymer to cause the diaphragm to change color when there is deformation of the diaphragm, and the first end of the tube is fluidly coupled to the conserver.

2. The portable apparatus of claim 1, wherein the receptacle is configured to be received within a pocket of a wearable garment.

3. The portable apparatus of claim 1, wherein the mouthpiece comprises a mixing chamber, the pressurized gas is pressurized oxygen, and the pressurized oxygen and the ambient air mix in the mixing chamber prior to entering into a mouth of a user.

4. The portable apparatus of claim 1, wherein the receptacle is refillable and capable of being moved with the user in a hands-free manner during vigorous activity, and wherein the conserver is configured to increase or decrease a flow of oxygen based on an activity level of the user.

5. The portable apparatus of claim 1, wherein:
    an opening in the mouthpiece fluidly coupling the second fluid channel to the ambient air is formed in a lateral side of the mouthpiece; and
    the mouthpiece includes a teeth engagement portion, a lip engagement portion, and a lip protection portion;
    the teeth engagement portion defining a mixing chamber therein.

6. The portable apparatus of claim 5, wherein the opening is elongated.

7. A portable apparatus for oxygen delivery comprising:
    (a) a receptacle defining a space containing high pressure oxygen, the receptacle including a pressure regulator configured to indicate a condition of the high pressure oxygen and a conserver removably coupled to the receptacle configured to increase or decrease a flow of oxygen based on an input from a user;
    (b) a mouthpiece including a teeth engagement portion including an inner surface and an outer surface, a lip engagement portion, a lip protection portion, and a plate removably coupled to the lip protection portion;

the teeth engagement portion being configured to be clenched by teeth of a user and including a mixing chamber;

the lip engagement portion being disposed between the teeth engagement portion and the lip protection portion and defining a first fluid channel;

the lip protection portion defining a second fluid channel fluidly coupled to ambient air and the mixing chamber and configured to allow ambient air to flow to the mixing chamber:

the plate being configured to restrict or allow ambient air to flow into the second fluid channel;

(c) a tube having a first end fluidly coupled to the receptacle and a second end fluidly coupled to the first fluid channel of the mouthpiece;

(d) the receptacle being configured to be received within a pocket of a wearable garment;

(e) wherein oxygen in the receptacle is allowed to flow to the mixing chamber via the tube and the first fluid channel upon inhalation of the user;

(f) wherein the receptacle includes a valve movable between a first position in which high pressure oxygen within the space is prevented from flowing to the pressure regulator, and a second position in which high pressure oxygen within the space is allowed to flow to the pressure regulator;

the valve comprising a biasing member coupled to a flange and a moveable pin;

wherein the valve is biased toward the first position via the high pressure oxygen;

the pin comprising a shaft and an arcuately shaped head;

the shaft extending through an opening of a plate; and a seal coupled to a surface of the head.

8. The portable apparatus of claim 7, wherein the ambient air and the oxygen mixes in the mixing chamber before entering into a mouth of the user.

9. The portable apparatus of claim 7, wherein the first end of the tube is fluidly coupled to the pressure regulator.

10. The portable apparatus of claim 7, wherein the lip protection portion comprises a pocket containing a filter, and ambient air flows through the filter prior to flowing through the second fluid channel.

11. The portable apparatus of claim 10, wherein the lip protection portion defines an opening fluidly coupling the second fluid channel to the ambient air, and the opening is formed in a lateral side of the lip protection portion.

12. The portable apparatus of claim 11, wherein the opening is elongated.

13. The portable apparatus of claim 7, wherein the lip engagement portion includes an oxygen bar protruding outwardly from a lateral side thereof and defining the first fluid channel.

14. The portable apparatus of claim 13, wherein a plurality of openings are formed in a surface of the oxygen bar adjacent the mixing chamber to provide oxygen flowing through the first fluid channel to the mixing chamber.

15. A portable apparatus comprising a fluid source coupled to a mouthpiece,
(a) the mouthpiece comprising:
a teeth engagement portion including a mixing chamber configured to be clenched by teeth of the user;
a lip engagement portion including a first fluid channel configured to be fluidly coupled to the fluid source;
a lip protection portion including a second fluid channel fluidly coupled to ambient air and the mixing chamber and configured to allow ambient air to flow to the mixing chamber; and
(b) the fluid source comprising a valve including a biasing member coupled to a flange and a moveable pin;
(c) oxygen being in the fluid source;
(d) the pin comprises a shaft and an arcuately shaped head; and
(e) the shaft extending through an opening of a plate and a seal is coupled to a surface of the head.

16. The apparatus of claim 15, further comprising a tube having a first end fluidly coupled to the fluid source, which includes a receptacle, and a second end fluidly coupled to the first fluid channel.

17. A portable apparatus comprising a fluid source coupled to a mouthpiece,
(a) the mouthpiece comprising:
a teeth engagement portion including a mixing chamber configured to be clenched by teeth of the user;
a lip engagement portion including a first fluid channel configured to be fluidly coupled to the fluid source;
a lip protection portion including a second fluid channel fluidly coupled to ambient air and the mixing chamber and configured to allow ambient air to flow to the mixing chamber;
(b) the fluid source comprising a valve including a biasing member coupled to a flange and a moveable pin;
(c) a conserver coupled to the fluid source;
the conserver comprising a pressure gauge including a metallic diaphragm located within a housing; and
the diaphragm being coated with a polymer to cause the diaphragm to change color when there is deformation of the diaphragm.

* * * * *